United States Patent
Chavarria et al.

(10) Patent No.: US 11,478,025 B2
(45) Date of Patent: Oct. 25, 2022

(54) THERAPEUTIC GARMENT

(71) Applicants: Miguel Chavarria, Torrance, CA (US); Carolina Chavarria, Torrance, CA (US)

(72) Inventors: Miguel Chavarria, Torrance, CA (US); Carolina Chavarria, Torrance, CA (US)

( * ) Notice: Subject to any disclaimer, the term of this patent is extended or adjusted under 35 U.S.C. 154(b) by 1029 days.

(21) Appl. No.: 16/176,676

(22) Filed: Oct. 31, 2018

(65) Prior Publication Data

US 2020/0128886 A1    Apr. 30, 2020

(51) Int. Cl.
| | |
|---|---|
| *A41D 13/005* | (2006.01) |
| *A41D 27/10* | (2006.01) |
| *A41D 27/24* | (2006.01) |
| *A61F 7/02* | (2006.01) |
| *A41D 1/04* | (2006.01) |
| *A61F 7/00* | (2006.01) |

(52) U.S. Cl.
CPC ........... *A41D 13/0053* (2013.01); *A41D 1/04* (2013.01); *A41D 27/10* (2013.01); *A41D 27/24* (2013.01); *A61F 7/02* (2013.01); *A41D 2300/32* (2013.01); *A41D 2300/50* (2013.01); *A41D 2400/32* (2013.01); *A61F 2007/0029* (2013.01); *A61F 2007/0279* (2013.01)

(58) Field of Classification Search
CPC ........ A61F 2007/0029; A61F 2007/003; A61F 2007/0031; A61F 2007/0032; A61F 2007/0034; A41D 13/0053
See application file for complete search history.

(56) References Cited

U.S. PATENT DOCUMENTS

| | | | | |
|---|---|---|---|---|
| 4,356,570 A | | 11/1982 | Vernon | |
| 4,569,087 A | * | 2/1986 | Kerwin | A41D 13/0053 2/69 |
| 4,603,440 A | * | 8/1986 | Hale | A41D 1/04 2/127 |
| 4,805,620 A | * | 2/1989 | Meistrell | A61F 7/08 607/108 |
| 4,976,262 A | * | 12/1990 | Palmacci | A61F 13/06 607/108 |
| 5,090,409 A | * | 2/1992 | Genis | A61F 7/08 D24/207 |
| 5,484,448 A | * | 1/1996 | Steele | A41D 13/0053 607/108 |
| 5,609,569 A | * | 3/1997 | Offenhartz | A61F 5/3746 602/61 |

(Continued)

*Primary Examiner* — Alissa L Hoey

(57) ABSTRACT

A therapeutic garment for cooling an arm of a user includes a vest that is configured to position over a torso of the user. A sleeve is coupled to and extends from a circumference of an armhole of the vest so that the sleeve is configured to insert the arm of the user. The sleeve comprises an inner layer that is coupled to an outer layer so that the inner layer and the outer layer define an interior space. The interior space extends from a cuff of the sleeve to the armhole. An orifice is positioned in the outer layer proximate to the armhole. The orifice is configured to selectively insert a cooling material into the interior space, positioning the cooling material to cool the arm of the user. A closure is coupled to the outer layer proximate to the orifice and is positioned to selectively and sealably close the orifice.

6 Claims, 5 Drawing Sheets

(56) References Cited

U.S. PATENT DOCUMENTS

| | | | | |
|---|---|---|---|---|
| 6,189,149 B1* | 2/2001 | Allen | ................. | A41D 13/0055 |
| | | | | 607/114 |
| 6,237,151 B1* | 5/2001 | Dellinger | ............... | A41D 13/08 |
| | | | | 2/69 |
| 6,654,968 B2* | 12/2003 | Braun | .................... | A41D 27/10 |
| | | | | 2/269 |
| 7,310,825 B2* | 12/2007 | St-Germain | ........... | A41D 27/10 |
| | | | | 2/125 |
| D674,106 S | 1/2013 | Hadash | | |
| 9,289,323 B2* | 3/2016 | Marton | .................... | A61F 7/02 |
| 9,427,033 B2 | 8/2016 | Blakely | | |
| 11,278,065 B2* | 3/2022 | Hubbs | ...................... | A41D 3/00 |
| 2002/0016984 A1* | 2/2002 | Poholski | ............ | A41D 13/0058 |
| | | | | 607/108 |
| 2004/0163154 A1 | 8/2004 | Cooper | | |
| 2004/0244412 A1* | 12/2004 | Trinh | ........................ | F25D 3/08 |
| | | | | 62/457.2 |
| 2009/0000002 A1 | 1/2009 | Hadash | | |
| 2010/0024088 A1 | 2/2010 | Griefer | | |
| 2010/0057173 A1* | 3/2010 | Leavitt | ...................... | A61F 7/10 |
| | | | | 607/114 |
| 2012/0031142 A1* | 2/2012 | Marton | ...................... | A61F 7/10 |
| | | | | 62/530 |
| 2014/0245527 A1* | 9/2014 | Douglas | ............ | A41D 13/0051 |
| | | | | 2/24 |
| 2016/0228288 A1* | 8/2016 | Nelson | .................. | A61F 13/143 |
| 2017/0086516 A1* | 3/2017 | Parenteau | ............ | A41D 13/087 |
| 2018/0185190 A1* | 7/2018 | Tilley | ........................ | A61F 7/10 |
| 2019/0298568 A1* | 10/2019 | Rayford, Sr. | .......... | A61F 5/0102 |
| 2020/0146879 A1* | 5/2020 | Varda | ........................ | A61F 7/10 |
| 2020/0214369 A1* | 7/2020 | Winningham | .......... | A61F 7/007 |
| 2020/0383408 A1* | 12/2020 | Riquetti | ............ | A41D 31/065 |
| 2020/0405531 A1* | 12/2020 | Juaire | ................ | A41D 13/0058 |
| 2021/0007888 A1* | 1/2021 | Rayford, Sr. | ............. | A61F 7/02 |
| 2022/0110393 A1* | 4/2022 | Isherwood | ............. | A41D 27/10 |

* cited by examiner

THERAPEUTIC GARMENT

CROSS-REFERENCE TO RELATED APPLICATIONS

Not Applicable

STATEMENT REGARDING FEDERALLY SPONSORED RESEARCH OR DEVELOPMENT

Not Applicable

The Names of the Parties to a Joint Research Agreement

Not Applicable

Incorporation-by-Reference of Material Submitted on a Compact Disc or as a Text File Via the Office Electronic Filing System Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relate to garments and more particularly pertains to a new garment for cooling an arm of a user.

BRIEF SUMMARY OF THE INVENTION

An embodiment of the disclosure meets the needs presented above by generally comprising a vest that is configured to position over a torso of a user. A sleeve is coupled to and extends from a circumference of an armhole of the vest so that the sleeve is configured to insert an arm of the user. The sleeve comprises an inner layer that is coupled to an outer layer so that the inner layer and the outer layer define an interior space. The interior space extends from a cuff of the sleeve to the armhole. An orifice is positioned in the outer layer proximate to the armhole. The orifice is configured to selectively insert a cooling material into the interior space, positioning the cooling material to cool the arm of the user. A closure is coupled to the outer layer proximate to the orifice and is positioned to selectively and sealably close the orifice.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
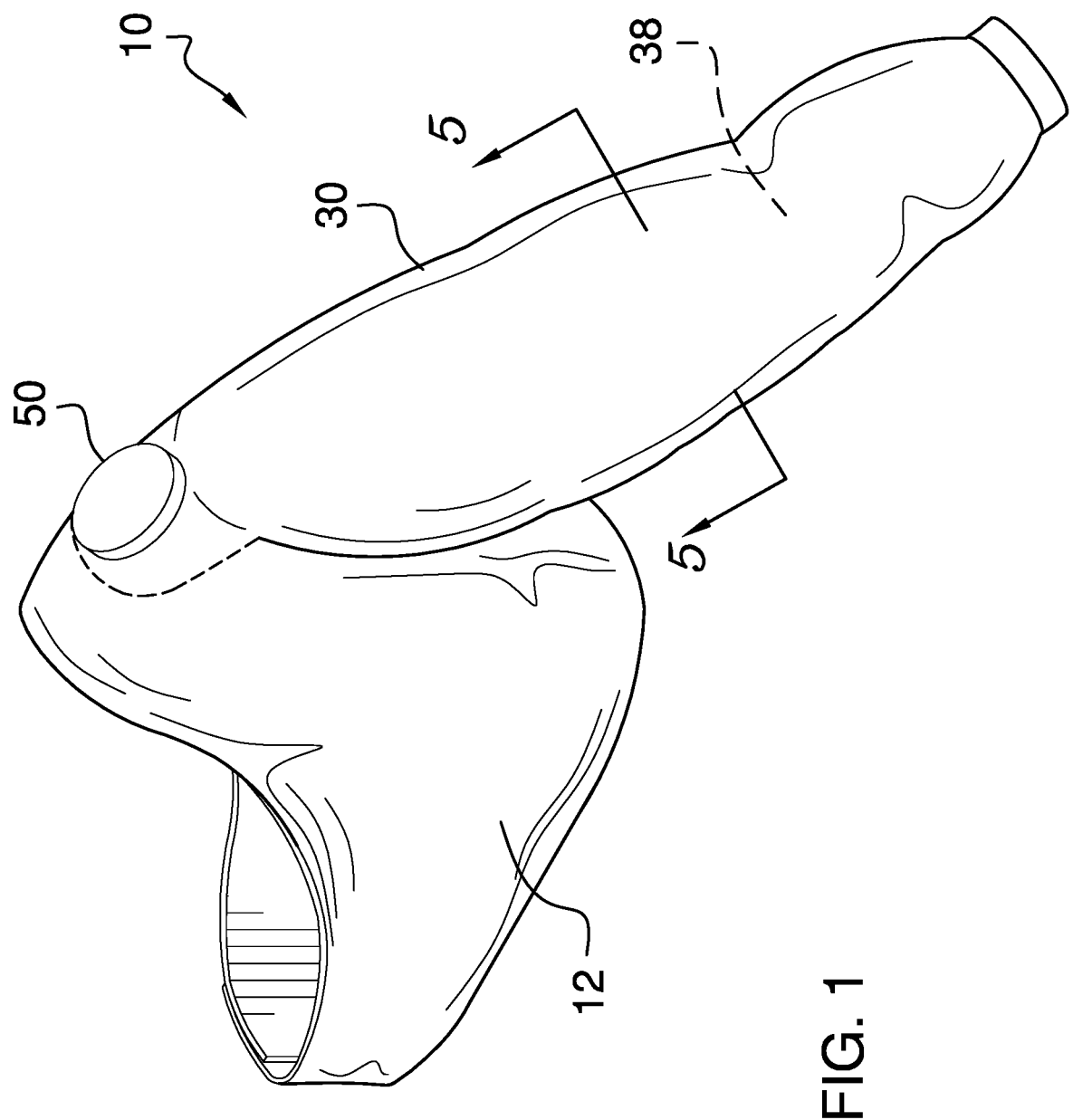
FIG. 1 is an isometric perspective view of a therapeutic garment according to an embodiment of the disclosure.

With reference now to the drawings, and in particular to FIGS. 1 through 5 thereof, a new garment embodying the principles and concepts of an embodiment of the disclosure and generally designated by the reference numeral 10 will be described.

Figure 2:
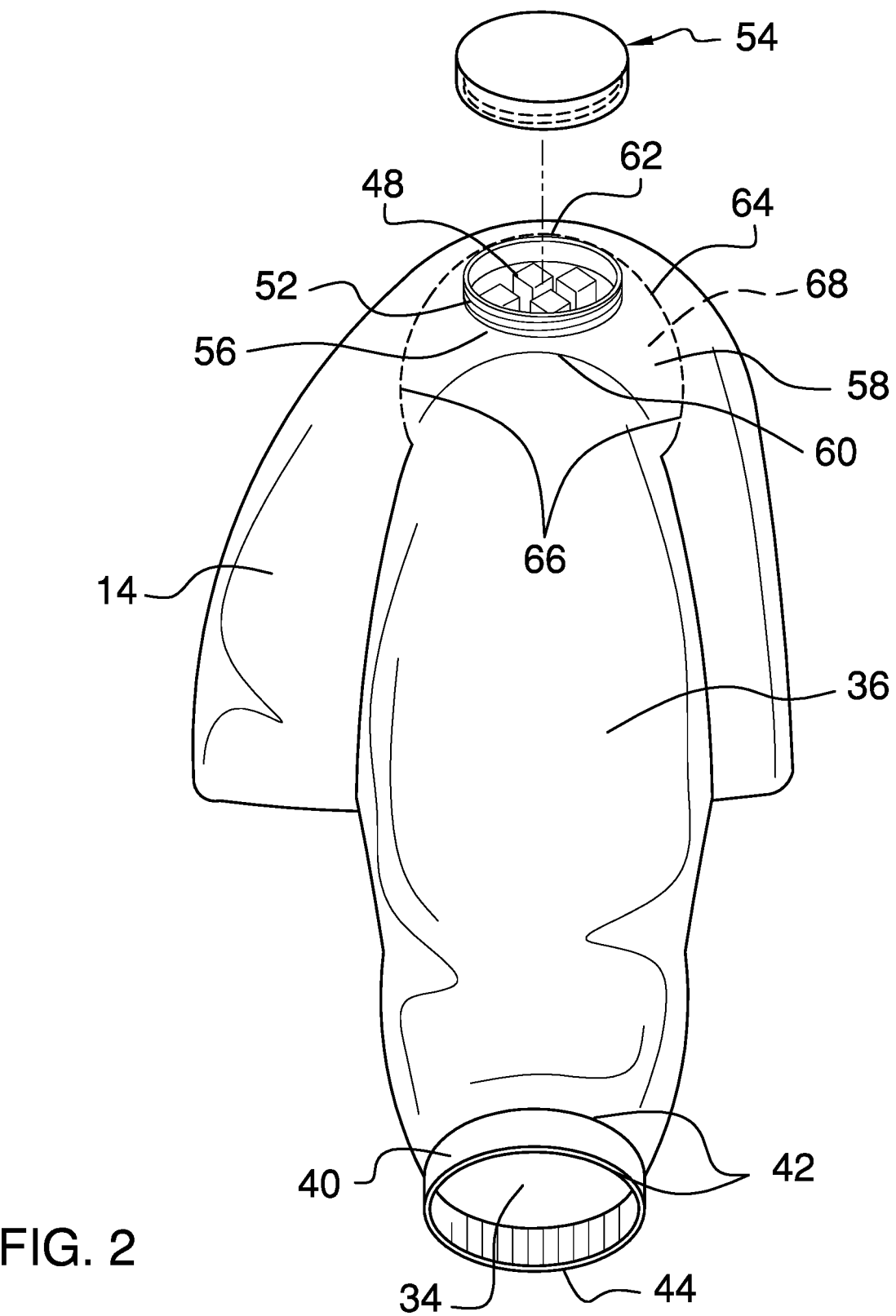
FIG. 2 is a side view of an embodiment of the disclosure.
Figure 3:
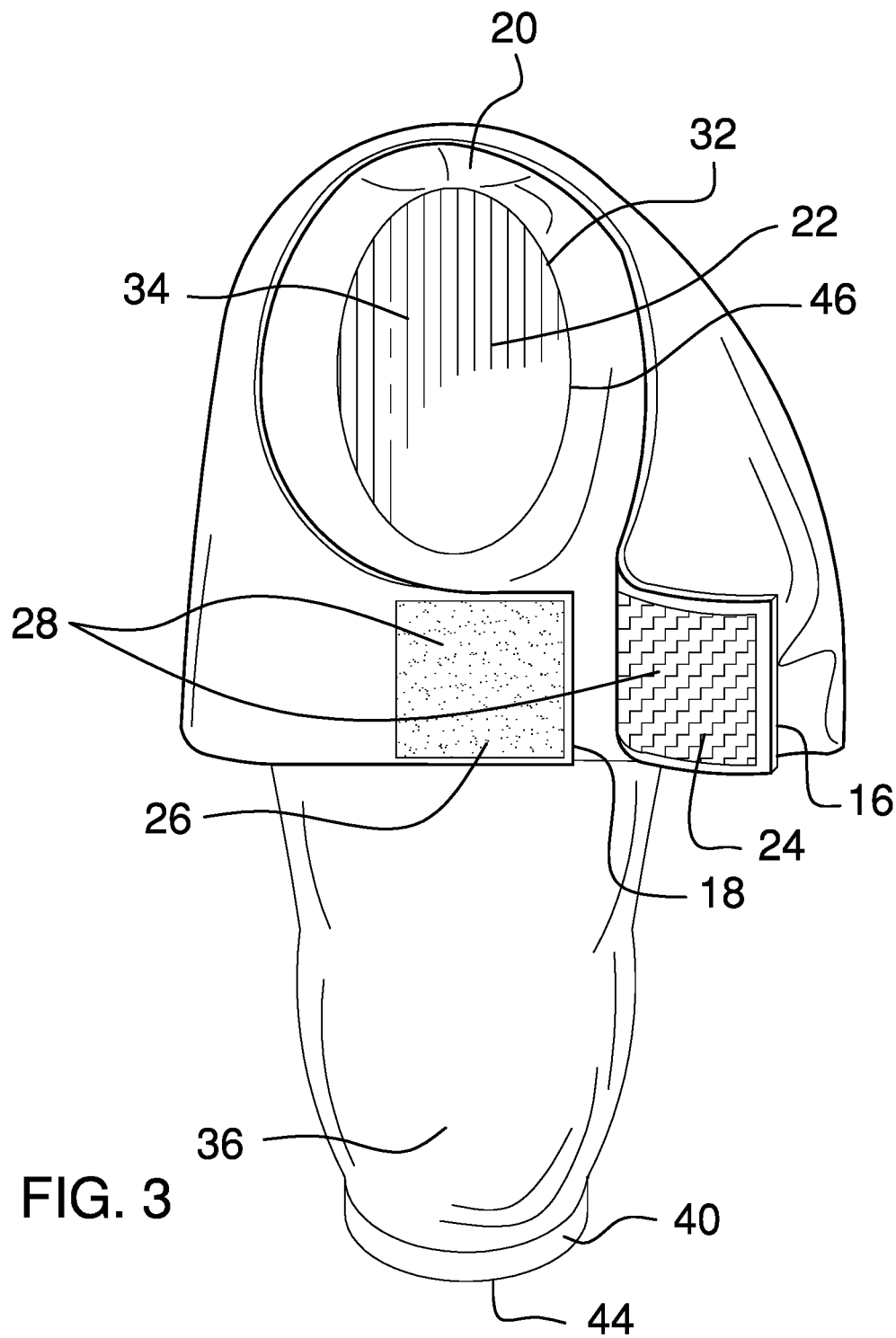
FIG. 3 is a side view of an embodiment of the disclosure.

As best illustrated in FIGS. 1 through 5, the therapeutic garment 10 generally comprises a vest 12 that is configured to position over a torso of a user. The vest 12 comprises a panel 14 that has a first end 16, a second end 18, and a center section 20. The center section 20 is shaped complementarily to a shoulder of the user. An armhole 22 positioned in the center section 20, as shown in FIG. 3.

Figure 4:
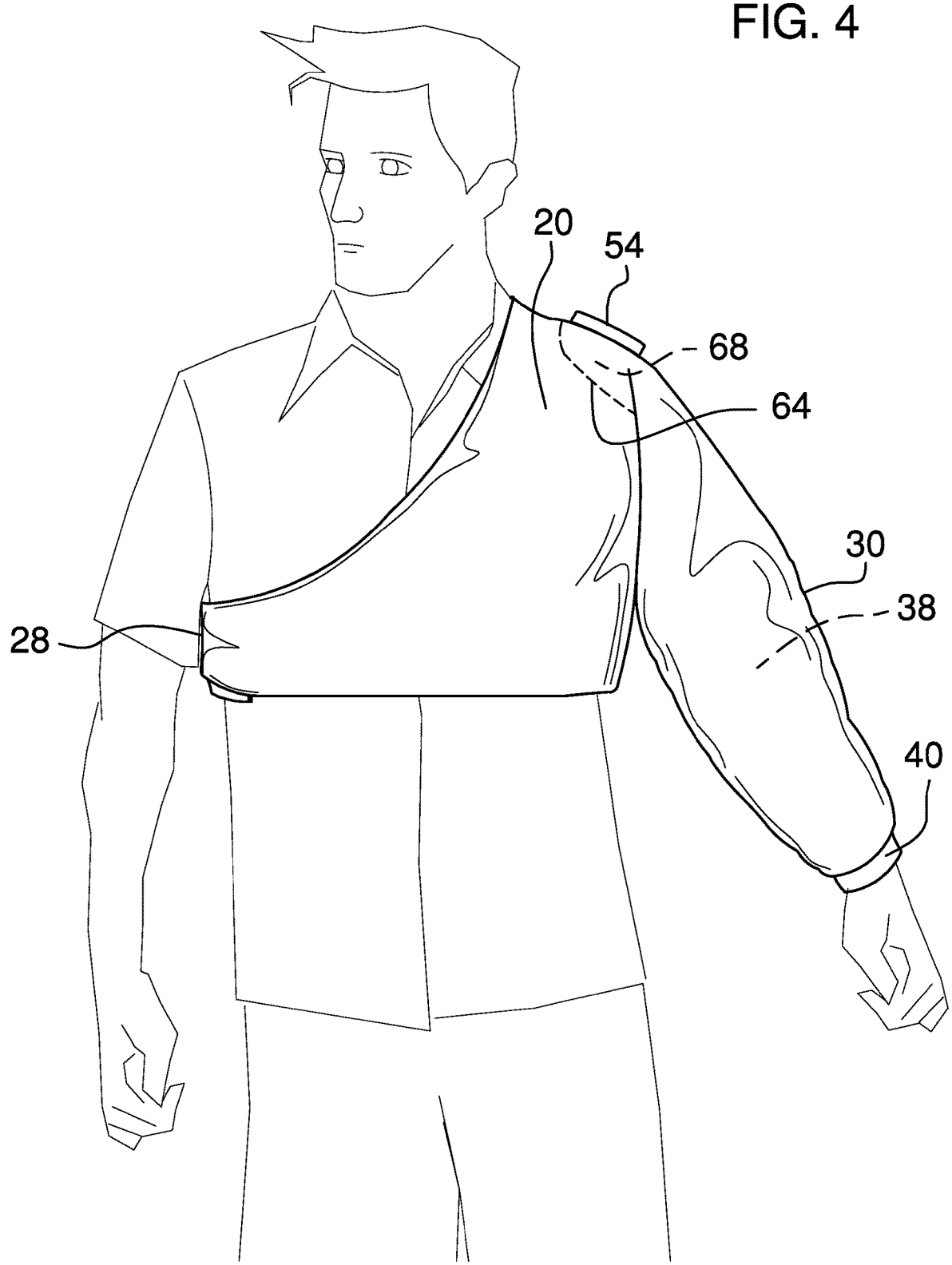
FIG. 4 is an in-use view of an embodiment of the disclosure.
Figure 5:
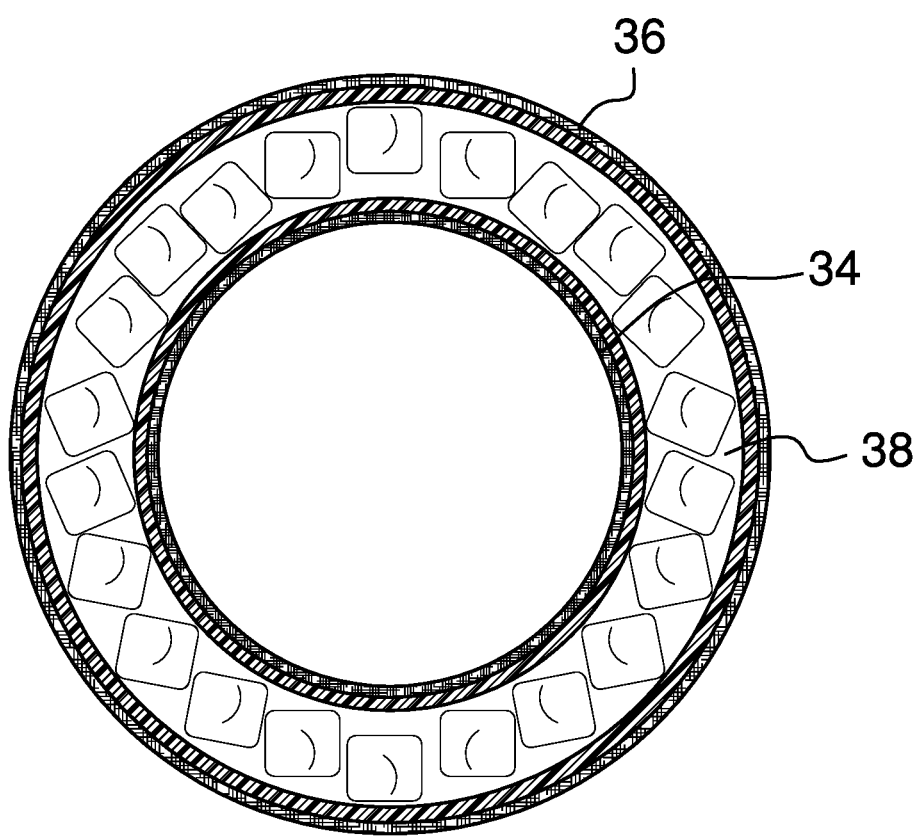
FIG. 5 is a cross-sectional view of an embodiment of the disclosure.

A first coupler 24 is coupled to the panel 14 proximate to the first end 16. A second coupler 26 is coupled to the panel 14 proximate to the second end 18. The second coupler 26 is complementary to the first coupler 24. The second coupler 26 is positioned to selectively couple to the first coupler 24 to couple the panel 14 around a torso of the user so that the center section 20 is positioned over the shoulder of the user and so that the panel 14 covers an upper region of the torso of the user, as shown in FIG. 4. The second coupler 26 and the first coupler 24 comprise a hook and loop fastener 28, as shown in FIG. 3.

A sleeve 30 is coupled to and extends from a circumference 32 of the armhole 22 of the vest 12 so that the sleeve 30 is configured to insert an arm of the user, as shown in FIG. 4. The sleeve 30 comprises an inner layer 34 is coupled to an outer layer 36 so that the inner layer 34 and the outer layer 36 define an interior space 38. The interior space 38 extends from a cuff 40 of the sleeve 30 to the armhole 22. The outer layer 36 is insulated. The inner layer 34 and the outer layer 36 comprise waterproof fabric.

A pair of first seams 42 is positioned in the sleeve 30 proximate a lower end 44 of the sleeve 30, as shown in FIG. 2. The first seams 42 couple the inner layer 34 to the outer layer 36 and define the cuff 40. A second seam 46 is coupled to the circumference 32 of the armhole 22, the inner layer 34, and the outer layer 36 so that the sleeve 30 is coupled to the vest 12.

An orifice 48, which is circularly shaped, is positioned in the outer layer 36 proximate to the armhole 22. The orifice 48 is configured to selectively insert a cooling material, such as ice, a gel pack, or the like, into the interior space 38, positioning the cooling material to cool the arm of the user.

The cooling of the arm can provide relief from muscle pain, joint pain, and swelling that may be caused by sporting activities, injury, arthritis, or the like.

A closure 50 is coupled to the outer layer 36 proximate to the orifice 48. The closure 50 is positioned to selectively and sealably close the orifice 48. The closure 50 comprises a ring 52 and a cap 54. The ring 52 is coupled to and extends from a perimeter 56 of the orifice 48. The ring 52 is externally threaded and the cap 54 is internally threaded so that the cap 54 is complementary to the ring 52. The cap 54 is positioned to selectively and threadedly couple to the ring 52 to sealably close the orifice 48.

In one embodiment, as shown in FIG. 2, the garment 10 comprises a flap 58 that has a first edge 60, which is coupled to the outer layer 36 so that a second edge 62 of the flap 58 extends past the armhole 22 and over the panel 14. In this embodiment, the second seam 46 couples the inner layer 34 to the armhole 22 around the entire circumference 32 of the armhole 22 and couples the outer layer 36 to the vest 12, except along the first edge 60 of the flap 58.

A third seam 64 extends from the first edge 60 of the flap 58 around opposing edges 66 and the second edge 62 of the flap 58 so that the flap 58 is coupled to the panel 14 to define a pouch 68. The pouch 68 is in fluidic communication with the interior space 38. In this embodiment, the orifice 48 is positioned in the flap 58. The orifice 48 is configured to selectively insert the cooling material into the pouch 68 and the interior space 38, positioning the cooling material to cool the shoulder and the arm of the user.

In use, the cooling material is inserted into the interior space 38 through the orifice 48 and the cap 54 is coupled to the ring 52 to close the orifice 48. The arm of the user is inserted into the sleeve 30. The hook and loop fastener 28 then is used to secure the panel 14 to the torso of the user to retain the sleeve 30 in position over the arm of the user. The cooling material is configured to cool the arm of the user to provide therapeutic relief.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the elements is present, unless the context clearly requires that there be only one of the elements.

We claim:

1. A therapeutic garment comprising:
a vest configured for positioning over a torso of a user;
a sleeve coupled to and extending from a circumference of an armhole of the vest, the sleeve comprising an inner layer coupled to an outer layer such that the inner layer and the outer layer define an interior space, the interior space extending from a cuff of the sleeve to the armhole wherein the sleeve is configured for inserting an arm of the user;
an orifice positioned in the outer layer proximate to the armhole wherein the orifice is configured for selectively inserting a cooling material into the interior space configuring the cooling material for cooling the arm of the user;
a closure coupled to the outer layer proximate to the orifice wherein the closure is positioned for selectively sealably closing the orifice;
the vest comprising:
a panel having a first end and a second end, the panel having a center section, the center section being configured to fit over a shoulder of the user, the armhole being positioned in the center section;
a first coupler coupled to the panel proximate to the first end; and
a second coupler coupled to the panel proximate to the second end, the second coupler being complementary to the first coupler wherein the second coupler is positioned for selectively coupling to the first coupler wherein the panel is configured for coupling around a torso of the user such that the center section is positioned over the shoulder of the user and such that the panel is configured to cover an upper region of the torso of the user;
a pair of first seams positioned in the sleeve proximate a lower end of the sleeve, the first seams coupling the inner layer to the outer layer defining the cuff;
a second seam coupled to the circumference of the armhole, the inner layer, and the outer layer such that the sleeve is coupled to the vest
a flap having a first edge, the first edge being coupled to the outer layer so that a second edge of the flap extends past the armhole and over the panel, the second seam coupling the inner layer to the armhole around the circumference of the armhole and coupling the outer layer to the vest except along the first edge of the flap; and
a third seam extending from the first edge of the flap around opposing edges and the second edge of the flap so that the flap is coupled to the panel to define a pouch, the pouch being in fluidic communication with the interior space, the orifice being positioned in the flap wherein the orifice is configured for selectively inserting the cooling material into the pouch and the interior space positioning the cooling material for cooling the shoulder and the arm of the user.

2. The garment of claim 1, further including the second coupler and the first coupler comprising a hook and loop fastener.

3. The garment of claim 1, further including the outer layer being insulated.

4. The garment of claim 3, further including the inner layer and the outer layer comprising waterproof fabric.

5. The garment of claim 1, further comprising:
the orifice being circularly shaped; and
the closure comprising:
a ring coupled to and extending from a perimeter of the orifice, the ring being externally threaded, and
a cap, the cap being internally threaded such that the cap is complementary to the ring wherein the cap is positioned for selectively threadedly coupling to the ring for sealably closing the orifice.

6. A therapeutic garment comprising:
a vest configured for positioning over a torso of a user, the vest comprising:
  a panel having a first end and a second end, the panel having a center section, the center section being configured to fit over a shoulder of the user,
  an armhole positioned in the center section,
  a first coupler coupled to the panel proximate to the first end, and
  a second coupler coupled to the panel proximate to the second end, the second coupler being complementary to the first coupler wherein the second coupler is positioned for selectively coupling to the first coupler for coupling the panel around a torso of the user such that the center section is positioned over the shoulder of the user and such that the panel covers an upper region of the torso of the user, the second coupler and the first coupler comprising a hook and loop fastener;
a sleeve coupled to and extending from a circumference of the armhole of the vest, the sleeve comprising an inner layer coupled to an outer layer such that the inner layer and the outer layer define an interior space, the interior space extending from a cuff of the sleeve to the armhole wherein the sleeve is configured for inserting an arm of the user, the outer layer being insulated, the inner layer and the outer layer comprising waterproof fabric;
a pair of first seams positioned in the sleeve proximate a lower end of the sleeve, the first seams coupling the inner layer to the outer layer defining the cuff;
a second seam coupled to the circumference of the armhole, the inner layer, and the outer layer such that the sleeve is coupled to the vest;
an orifice positioned in the outer layer proximate to the armhole wherein the orifice is configured for selectively inserting a cooling material into the interior space configuring the cooling material for cooling the arm of the user, the orifice being circularly shaped;
a closure coupled to the outer layer proximate to the orifice wherein the closure is positioned for selectively sealably closing the orifice; the closure comprising:
  a ring coupled to and extending from a perimeter of the orifice, the ring being externally threaded, and
  a cap, the cap being internally threaded such that the cap is complementary to the ring wherein the cap is positioned for selectively threadedly coupling to the ring for sealably closing the orifice;
a flap having a first edge, the first edge being coupled to the outer layer so that a second edge of the flap extends past the armhole and over the panel, the second seam coupling the inner layer to the armhole around the circumference of the armhole and coupling the outer layer to the vest except along the first edge of the flap; and
a third seam extending from the first edge of the flap around opposing edges and the second edge of the flap so that the flap is coupled to the panel to define a pouch, the pouch being in fluidic communication with the interior space, the orifice being positioned in the flap wherein the orifice is configured for selectively inserting the cooling material into the pouch and the interior space positioning the cooling material for cooling the shoulder and the arm of the user.

\* \* \* \* \*